United States Patent
Xu et al.

(10) Patent No.: US 9,738,603 B2
(45) Date of Patent: Aug. 22, 2017

(54) COMPLEX OF GLUCOSE DERIVATIVE AND PROLINE, CRYSTAL, PREPARATION METHOD AND USE

(71) Applicant: SHANGHAI YINGLI PHARMACEUTICAL CO., LTD., Shanghai (CN)

(72) Inventors: Zusheng Xu, Shanghai (CN); Bin Shi, Shanghai (CN); Hongwei Ren, Shanghai (CN)

(73) Assignee: SHANGHAI YINGLI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 14/758,289

(22) PCT Filed: Dec. 30, 2013

(86) PCT No.: PCT/CN2013/090856
§ 371 (c)(1),
(2) Date: Jun. 29, 2015

(87) PCT Pub. No.: WO2014/101865
PCT Pub. Date: Jul. 3, 2014

(65) Prior Publication Data
US 2015/0336888 A1    Nov. 26, 2015

(30) Foreign Application Priority Data
Dec. 31, 2012 (CN) .......................... 2012 1 0594549

(51) Int. Cl.
*C07D 207/16* (2006.01)

(52) U.S. Cl.
CPC ........ *C07D 207/16* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 6,414,126 B1 | 7/2002 | Ellsworth et al. |
| 6,515,117 B2 | 2/2003 | Ellsworth et al. |
| 6,774,112 B2 | 8/2004 | Gougoutas |
| 7,375,213 B2 | 5/2008 | Deshpande et al. |
| 7,838,498 B2 | 11/2010 | Chen et al. |
| 7,838,499 B2 | 11/2010 | Chen et al. |
| 7,858,587 B2 | 12/2010 | Eckhardt et al. |
| 7,919,598 B2 | 4/2011 | Gougoutas et al. |
| 7,932,379 B2 | 4/2011 | Deshpande et al. |
| 7,943,748 B2 | 5/2011 | Matsuoka et al. |
| 8,097,592 B2 | 1/2012 | Imamura et al. |
| 8,106,021 B2 | 1/2012 | Chen et al. |
| 8,202,984 B2 | 6/2012 | Nomura et al. |
| 8,222,219 B2 | 7/2012 | Nomura et al. |
| 8,501,698 B2 | 8/2013 | Gougoutas et al. |
| 8,575,321 B2 | 11/2013 | Chen et al. |
| 8,802,637 B2 | 8/2014 | Chen et al. |
| 8,980,829 B2 | 3/2015 | Xu et al. |
| 2002/0137903 A1 | 9/2002 | Ellsworth et al. |
| 2003/0064935 A1 | 4/2003 | Gougoutas |

(Continued)

FOREIGN PATENT DOCUMENTS

| | | |
|---|---|---|
| CN | 103910769 A | 7/2014 |
| WO | 0127128 A1 | 4/2001 |

(Continued)

OTHER PUBLICATIONS

International Search Report dated Mar. 27, 2014 issued in corresponding PCT/CN2013/090856 application (pp. 1-8).
International Search Report dated Mar. 27, 2014 issued in corresponding PCT/CN2013/090856 application (pp. 1-9).
Written Opinion of the International Searching Authority dated Mar. 27, 2014 issued in corresponding PCT/CN2013/090856 application (pp. 1-9).
A.L. Handlon et al., "Sodium glucose co-transporter 2 (SGLT2) inhibitors as potentioal antidiabetic agents", Expert Opin. Ther. Patents, vol. 15, No. 11 (2005) pp. 1531-1540.
W. N. Washburn, "Development of the Renal Glucose Reabsorption Inhibitors: A New Mechanism for the Pharmacotherapy of Diabetes Mellitus Type 2", Journal of Medicinal Chemistry, vol. 52, No. 7 (2009) pp. 1785-1794.
E. C. Chao et al., "SGLT2 inhibition—a novel strategy for diabetes treatment", Nature Reviews Drug Discovery, vol. 9, No. 7 (2010) pp. 551-559.

(Continued)

*Primary Examiner* — Layla Berry
*Assistant Examiner* — Bahar Craigo
(74) *Attorney, Agent, or Firm* — Millen White Zelano and Branigan, PC; John Sopp; Anthony Zelano

(57) ABSTRACT

Disclosed are a complex of glucose derivative and proline, a crystal, a preparation method and a use. In an X-ray powder diffraction diagram of the eutectic crystal when the diffraction angle is 2θ, characteristic diffraction peaks comprise 4.339, 11.499, 12.835, 13.921, 15.294, 16.212, 16.804, 17.154, 18.335, 19.274, 19.982, 22.710, 23.218, 24.885, 27.940, 29.612 and 30.313, and the 2θ error range is ±0.1. The method comprises: mixing a compound A solution with an L-proline solution, and performing cooling and crystallization. The present invention further provides a of the crystal in medicine preparation. The eutectic crystal in the present invention features high water-solubility, low hygroscopicity and high stability, and is suitable for manufacturing a variety of preparations.

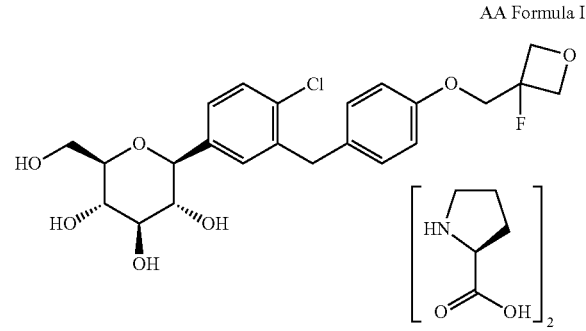

AA Formula I

11 Claims, 3 Drawing Sheets

(56) References Cited

U.S. PATENT DOCUMENTS

| | | |
|---|---|---|
| 2003/0114390 A1 | 6/2003 | Washburn et al. |
| 2004/0138439 A1 | 7/2004 | Deshpande et al. |
| 2005/0209166 A1 | 9/2005 | Eckhardt et al. |
| 2005/0233988 A1 | 10/2005 | Nomura et al. |
| 2006/0122126 A1 | 6/2006 | Imamura et al. |
| 2007/0238866 A1 | 10/2007 | Deshpande et al. |
| 2007/0293690 A1 | 12/2007 | Tomiyama et al. |
| 2008/0004336 A1 | 1/2008 | Gougoutas et al. |
| 2008/0242596 A1 | 10/2008 | Chen et al. |
| 2008/0319047 A1 | 12/2008 | Matsuoka et al. |
| 2009/0118201 A1 | 5/2009 | Chen et al. |
| 2009/0143316 A1 | 6/2009 | Imamura et al. |
| 2009/0318547 A1 | 12/2009 | Eckhardt et al. |
| 2011/0105424 A1 | 5/2011 | Nomura et al. |
| 2011/0172176 A1 | 7/2011 | Gougoutas et al. |
| 2011/0201795 A1 | 8/2011 | Deshpande et al. |
| 2011/0207661 A1 | 8/2011 | Chen et al. |
| 2012/0058941 A1 | 3/2012 | Nomura et al. |
| 2012/0329732 A1 | 12/2012 | Chen et al. |
| 2013/0303467 A1 | 11/2013 | Gougoutas et al. |
| 2013/0324464 A1 | 12/2013 | Xu et al. |
| 2014/0031300 A1 | 1/2014 | Chen et al. |
| 2014/0243517 A1 | 8/2014 | Deshpande et al. |

FOREIGN PATENT DOCUMENTS

| | | |
|---|---|---|
| WO | 02083066 A1 | 10/2002 |
| WO | 03099836 A1 | 12/2003 |
| WO | 2004063209 A1 | 7/2004 |
| WO | 2005012326 A1 | 2/2005 |
| WO | 2006011502 A1 | 2/2006 |
| WO | 2007114475 A1 | 10/2007 |
| WO | 2008002824 A1 | 1/2008 |
| WO | 2008034859 A1 | 3/2008 |
| WO | 2008122014 A1 | 10/2008 |
| WO | 2009026537 A1 | 2/2009 |
| WO | 2012109996 A1 | 8/2012 |

OTHER PUBLICATIONS

European Patent Application EP13866998.1 (not published); English Translation of CN 103910769 dated Jul. 9, 2014.
EP Office Action dated Oct. 12, 2016, issued in corresponding EP Application No. 13 866 998.1-1454, 4 pages.

COMPLEX OF GLUCOSE DERIVATIVE AND PROLINE, CRYSTAL, PREPARATION METHOD AND USE

The present application is the U.S. national stage application of International Application PCT/CN2013/090856, filed Dec. 30, 2013, which international application was published on Jul. 3, 2014, as International Publication WO2014/101865A1. The International Application claims priority of Chinese Patent Application 201210594549.9, filed Dec. 31, 2012, the contents of which are incorporated herein by reference in their entireties.

FIELD OF INVENTION

The present invention relates to a complex of a glucose derivative and proline, eutectic crystal, preparation method and use; in particular to a complex of (2S,3R,4R,5S,6R)-2-(4-chloro-3-(4-((3-fluorooxetan-3-yl)methoxy)benzyl)phenyl)-6-(hydroxymethyl)tetrahydro-2H-pyran-3,4,5-triol and bis(L-proline), eutectic crystal, preparation method and use.

PRIOR ARTS

Sodium-dependent glucose co-transporters (SGLTs) play a key role in maintaining human plasma glucose stable. SGLTs have been found in intestine (SGLT1) and kidney (SGLT1 and SGLT2). Renal SGLT reabsorbs glucose from renal filtrate, thereby preventing the loss of glucose from urine. 98% of glucose is reabsorbed in the kidney by SGLT2, and only the remaining 2% is reabsorbed by SGLT1. Inhibition of SGLT2 can specifically inhibit the re-absorption of glucose by kidney and increase the excretion of glucose in the urine, which may normalize the plasma glucose for diabetics. Therefore, the inhibitors of SGLT, particularly SGLT2, are promising candidates for anti-diabetic drugs (Handlon, A. L., Expert Opin. Ther. Patents (2005) 15(11): 1531-1540).

So far, a lot of pharmaceutical companies have developed a series of SGLT2 inhibitors, such as those described in: Handlon, A. L., Expert Opin. Ther. Patents (2005) 15(11): 1531-1540; William N. W., Journal of Medicinal Chemistry, 2009, Vol. 52, No. 7, 1785-1794; Chao, E. C. et al., Nature Reviews Drug Discovery, 2010, Vol. 9, No. 7, 551-559. Aryl glycosides as SGLT2 inhibitors are also known by the following patent applications: WO 01/27128, WO 02/083066, WO 03/099836, US 2003/0114390, WO 04/063209, WO 2005/012326, US 2005/0209166, US 2006/0122126, WO 2006/011502, US 2007/0293690, WO 2008/034859, WO 2008/122014 and WO 2009/026537.

A SGLT2 inhibitor (2S,3R,4R,5S,6R)-2-(4-chloro-3-(4-((3-fluorooxetan-3-yl)methoxy)benzyl)phenyl)-6-(hydroxymethyl)tetrahydro-2H-pyran-3,4,5-triol (hereinafter, referred to as "compound A") is described in an international patent application WO2012/109996 and has a chemical structure of formula A:

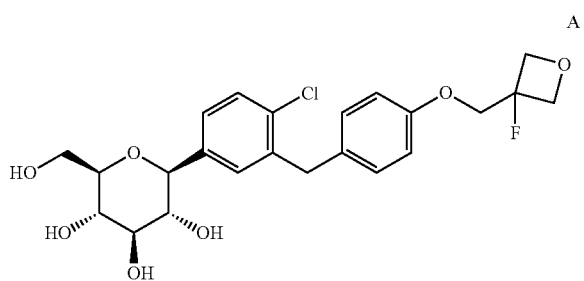 [SMILES: OC[C@H]1O[C@@H](c2ccc(Cl)c(Cc3ccc(OCC4(F)COC4)cc3)c2)[C@H](O)[C@@H](O)[C@@H]1O]

The compound A prepared by a method described in the patent is amorphous and hygroscopic, which gains 14.72% weight under 95% RH. After absorption of moisture, it is allochroic usually and easy to lose stability and decompose, which is not conducive to the operation of preparation. Therefore, it is necessary to develop an eutectic crystal of the compound A with excellent physical and chemical properties and is conducive to the operation of preparation.

CONTENT OF THE PRESENT INVENTION

The technical problem to be solved by the present invention is to provide a complex of a glucose derivative and proline, crystal, preparation method and use. The eutectic crystal of the glucose derivative (compound A) and proline in the present invention has better physical and chemical properties, better water solubility, lower hygroscopicity, higher stability and is particularly suitable for the preparation of various preparations. The structure of compound A is as follows:

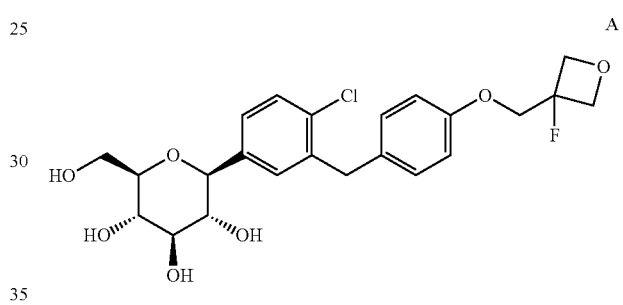

During the study of preparing the eutectic crystal of compound A, the inventors of the present invention have found that it can only afford jelly, oil or amorphous substance, etc. other than the eutectic crystal of compound A with good physical and chemical properties by using most of organic acids and inorganic acids commonly used in pharmacy. After continuously experiment, summarizing and improving, the inventors of the present invention have surprisingly found that when using L-proline, in particular to some special preparation conditions, the eutectic crystal of complex of (2S,3R,4R,5S,6R)-2-(4-chloro-3-(4-((3-fluorooxetan-3-yl)methoxy)benzyl)phenyl)-6-(hydroxymethyl)tetrahydro-2H-pyran-3,4,5-triol and bis(L-proline) (hereinafter, referred to as "compound A·L-proline eutectic crystal") with excellent physical and chemical properties can be obtained. The crystal type of the eutectic crystal can be identified by its characteristic X-ray powder diffraction (XRPD).

The present invention provides a complex represented by formula I formed by a glucose derivative and L-proline, the complex is composed of compound A represented by formula A and L-proline, a molar ratio of compound A to L-proline is 1:2;

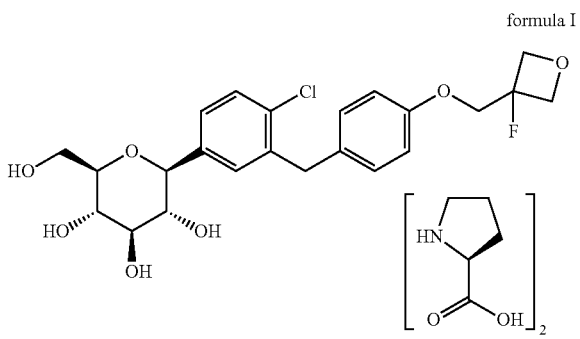

formula I

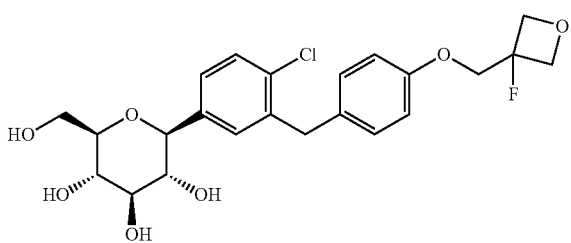

A

The complex refers to an aggregate formed by a series of molecules (e.g. complex organic compounds, inorganic compounds) and simple substance and with a certain (physiological and chemical) functionality or obvious (physical and chemical) characteristics.

The present invention also provides an eutectic crystal of above complex formed by the glucose derivative and L-proline,

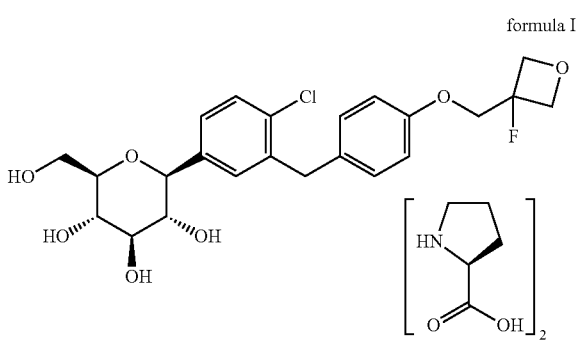

formula I

An X-ray powder diffraction diagram of the eutectic crystal shows characterized peaks at 4.339±0.1, 15.294±0.1, 16.804±0.1, 18.335±0.1, 19.274±0.1, 19.982±0.1, 23.218±0.1 and 24.885±0.1 when diffraction angle is 2θ and under Cu-Kα1 radiation.

The present invention also provides an eutectic crystal of above complex formed by the glucose derivative and L-proline,

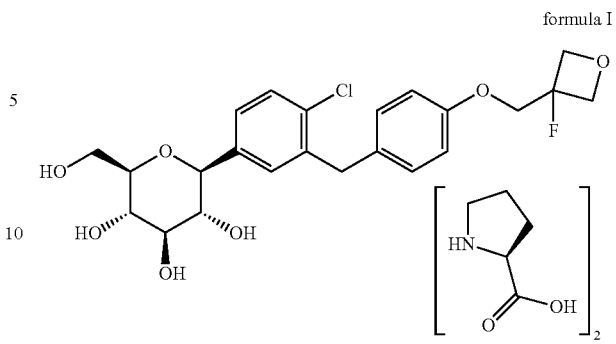

formula I

An X-ray powder diffraction diagram of the eutectic crystal shows characterized peaks at 4.339±0.1, 11.499±0.1, 12.835±0.1, 13.921±0.1, 15.294±0.1, 16.212±0.1, 16.804±0.1, 17.154±0.1, 18.335±0.1, 19.274±0.1, 19.982±0.1, 22.710±0.1, 23.218±0.1, 24.885±0.1, 27.940±0.1, 29.612±0.1 and 30.313±0.1 when diffraction angle is 2θ and under Cu-Kα1 radiation.

The present invention also provides a preparation method for preparing above eutectic crystal of the complex formed by the glucose derivative and L-proline, which comprises following steps: mixing a solution containing compound A with a solution containing L-proline, cooling and crystallization;

A wherein a solvent of the solution containing L-proline is 95% aqueous ethanol.

The preparation method preferably further comprises filtering the solution containing compound A with microporous membrane, and then mixing the filtrate with the solution containing L-proline. The microporous membrane is preferably nylon membrane with a pore size of 0.45 μm.

Usually, the solution containing compound A and the solution containing L-proline is mixed at a temperature of 30° C.-130° C., preferably 50° C.-110° C., more preferably 70° C.-90° C.

In the preparation method, the solution containing compound A can be prepared by following steps: mixing compound A with a solvent and forming the solution containing compound A. Preferably, compound A and the solvent is mixed under heating. The heating generally refers to make the temperature higher than ambient temperature, which aims to make compound A dissolve in the solvent completely, and generally heating temperature is 30° C.-130° C., preferably 50° C.-110° C., more preferably 70° C.-90° C.

In the preparation method, the solution containing L-proline can be prepared by following steps: mixing L-proline with 95% aqueous ethanol and forming the solution containing L-proline. Preferably, the amount of the 95% aqueous ethanol is 90 mg/mL-120 mg/mL relative to the mass of L-proline. Wherein, the percentage is a mass percentage.

A solvent of the solution containing compound A may be with polarity, low toxicity and moderate volatility, which can be easily miscible with 95% aqueous ethanol and is good for dissolving compound A, preferably it is selected from the group consisting of acetone, ethyl acetate, ethanol, water and acetonitrile. In the solution containing compound A, an amount of the solvent which should ensure dissolving compound A is controlled by a concentration of the solution containing compound A generally ranging from 25 mg/mL-400 mg/mL, preferably 50 mg/mL-300 mg/mL.

In the preparation method, a molar ratio of L-proline to compound A is 1-2.

The mixing may adopt common methods in the art, such as vortex mixing, magnetic mixing or turbulence mixing etc. The mixing generally lasts 1-30 mins, preferably 1-10 mins.

The cooling may refer to natural cooling or rapid cooling. The rapid cooling, typically, is to cool the reaction system rapidly by an ice-water bath or an ice-salt bath, etc.

The cooling which should make the eutectic crystal of the complex formed by compound A and L-proline precipitate is generally cooling to room temperature. In the present invention, the room temperature refers to ambient temperature, which is generally 10° C.-30° C. as defined in pharmacopoeia.

The rate of the cooling is preferably 1~20° C./h, more preferably 5~10° C./h, wherein a high cooling rate accelerates the crystallization process but forms the crystal with small particle size, while a slow cooling rate is conducive to the growth of the crystal and forming a perfect lattice.

In the preparation method of the present invention, the steps are preferably carried out under stirring. When the cooling and crystallization are carried out under stirring, temperature of the upper, middle and lower portion of the solution can be uniform, which is conducive to the uniformity of the crystal.

After precipitating, the eutectic crystal of the complex formed by compound A and L-proline can be separated by conventional methods in the art, usually comprising filtering, washing and drying. The filtering can refer to suction filtration. The conditions and procedures of the filtering can refer to conventional filtration operations in the art. The solvent used for the washing is preferably n-heptane. The drying may adopt conventional methods in the art, such as drying at atmospheric pressure or drying under reduced pressure. The temperature of the drying is preferably 40° C.

The eutectic crystal of the present invention when used as a pharmaceutically active substance is preferably in a substantially pure form, that is substantially free of other forms of crystal formed by compound A and L-proline. Unless otherwise specified, the present invention also covers a mixture of the eutectic crystal of the complex formed by compound A and L-proline as provided in the present application and one or more other polycrystals of the complex formed by compound A and L-proline. Once the pharmaceutically active substance is a mixed eutectic crystal, more preferably, the mixed eutectic crystal comprises at least 50% of the eutectic crystal of the complex formed by compound A and L-proline provided by the present application, wherein the percentage is a mass fraction.

The present invention further provides a use of the eutectic crystal of the complex of formula I formed by the glucose derivative and L-proline in preparing a medicament used for treating and/or preventing diseases and/or symptoms induced by the sodium-dependent glucose transporter SGLT (specifically SGLT2).

In addition, the present invention also provides a use of the eutectic crystal of the complex of formula I formed by the glucose derivative and L-proline in preparing a medicament used for treating and/or preventing metabolic disorders.

The metabolic disorders generally refer to: type 1 diabetes, type 2 diabetes, diabetic complications, metabolic acidosis or ketoacidosis, reactive hypoglycemia, hyperinsulinemia, glucose metabolic disorders, insulin resistance, metabolic syndrome, dyslipidemia caused by different reasons, atherosclerosis and related diseases, obesity, hypertension, chronic heart failure, edema and hyperuricemia.

The present invention also provides a use of the eutectic crystal of the complex of formula I formed by the glucose derivative and L-proline in preparing a medicament used for preventing the degeneration of pancreatic β-cells, or a medicament used for improving and/or restoring the functionality of pancreatic β-cells.

Without departing from the basis of knowledge in the art, each of the above preferred conditions can be any combination to afford the preferred embodiment of the present invention.

The related materials and reagents in the present invention are commercially available.

The positive effect of the present invention is that: in the present invention, the complex formed by compound A and L-proline is prepared successfully for the first time. Its eutectic crystal has excellent physical and chemical properties, high water solubility, low hygroscopicity, high stability, which is particularly suitable for preparing various pharmaceutical formulations containing compound A. The preparation method of the present invention is simple and convenient, suitable for industrial production.

DETAILED DESCRIPTION OF THE PREFERRED EMBODIMENT

Figure 1:
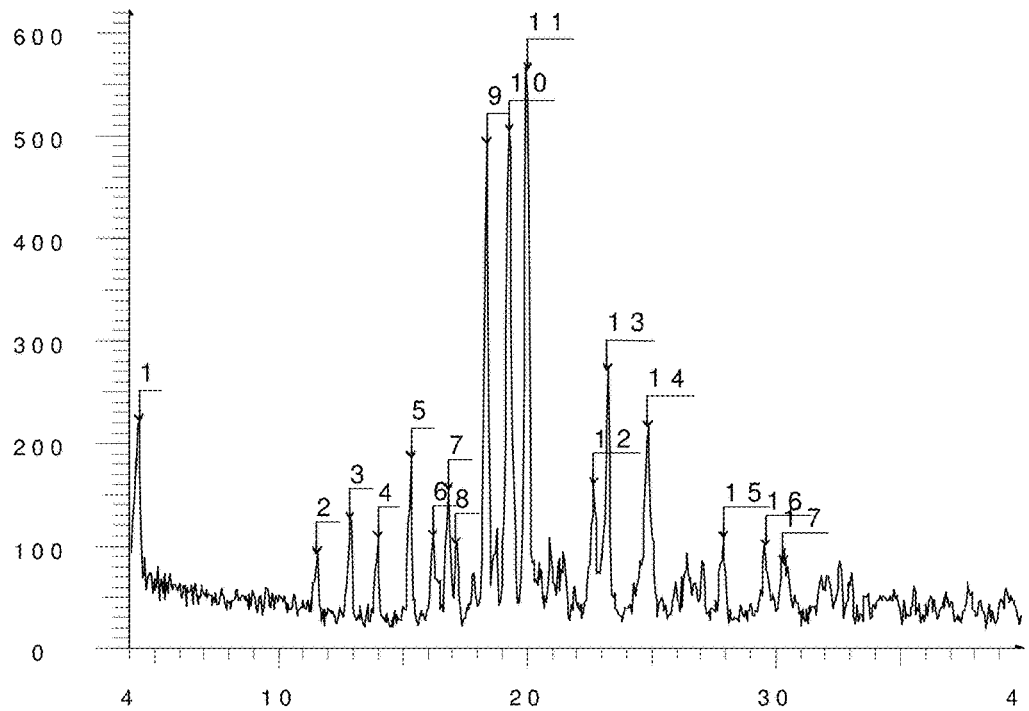
FIG. 1 is the X-ray powder diffraction diagram of the eutectic crystal of the complex formed by compound A and L-proline in effect example 1.

The following embodiments further illustrate the present invention, but the present invention is not limited thereto.

When an experimental condition is not specified in the following examples, conventional methods and conditions can be used, or can be selected from the product manual.

Compound A in the following example could be prepared with a prior method, such as the method disclosed in WO2012/109996.

Example 1 Preparation of the Eutectic Crystal of the Complex Formed by Compound A and L-Proline Compound A (25.0 mg) was dissolved in acetone (1 mL) and heated to 30° C. with magnetic stirring until compound A fully dissolved. The solution was filtered with a 0.45 μm microporous membrane (nylon membrane) and the filtrate was placed on a heater at 30° C. An equimolar ratio of 1 mol/L a solution containing L-proline in 95% aqueous ethanol (53.4 μL) was added slowly under magnetic stirring. The solution turned turbid and white solid began to precipitate after 5 minutes magnetic stirring, and then the mixture was cooled down to room temperature at a rate of 10° C./h under stirring, meanwhile a large amount of white precipitate appeared. The precipitated white solid was isolated from the suspension via vacuum filtration, and rinsed with n-heptane once. The product was then placed in a vacuum oven and dried under reduced pressure at 40° C. to obtain the final product.

Example 2 Preparation of the Eutectic Crystal of the Complex Formed by Compound A and L-Proline Compound A (25.0 mg) was dissolved in acetone (1 mL) and heated to 35° C. with magnetic stirring until compound A fully dissolved. The solution was filtered with a 0.45 μm microporous membrane (nylon membrane) and the filtrate was placed on a heater at 35° C. A 2-fold molar ratio of 1 mol/L a solution containing L-proline in 95% aqueous ethanol (106.8 μL) was added slowly under magnetic stirring. The solution turned turbid and white solid began to precipitate after 10 minutes magnetic stirring, and then the mixture was cooled down to room temperature at a rate of 15° C./h under stirring, meanwhile a large amount of white precipitate appeared. The precipitated white solid was isolated from the suspension via vacuum filtration, and rinsed with n-heptane twice. The product was then placed in a vacuum oven and dried under reduced pressure at 40° C. to obtain the final product.

Example 3 Preparation of the Eutectic Crystal of the Complex Formed by Compound A and L-Proline Compound A (25.0 mg) was dissolved in acetonitrile (1 mL) and heated to 30° C. with magnetic stirring until compound A fully dissolved. The solution was filtered with a 0.45 μm microporous membrane (nylon membrane) and the filtrate was placed on a heater at 30° C. An equimolar ratio of 1 mol/L a solution containing L-proline in 95% aqueous ethanol (53.4 μL) was added slowly under magnetic stirring. The solution turned turbid after 10 minutes magnetic stirring, and then the mixture was cooled down to room temperature at a rate of 10° C./h under stirring, meanwhile a large amount of white precipitate appeared. The precipitated white solid was isolated from the suspension via vacuum filtration, and rinsed with n-heptane once. The product was then placed in a vacuum oven and dried under reduced pressure at 40° C. to obtain the final product.

Example 4 Preparation of the Eutectic Crystal of the Complex Formed by Compound A and L-Proline Compound A (25.0 mg) was dissolved in acetonitrile (1 mL) and heated to 45° C. with magnetic stirring until compound A fully dissolved. The solution was filtered with a 0.45 μm microporous membrane (nylon membrane) and the filtrate was placed on a heater at 45° C. A 2-fold molar ratio of 1 mol/L a solution containing L-proline in 95% aqueous ethanol (106.8 μL) was added slowly under magnetic stirring. The solution turned turbid after 15 minutes magnetic stirring, and then the mixture was cooled down to room temperature at a rate of 15° C./h under stirring, meanwhile a large amount of white precipitate appeared. The precipitated white solid was isolated from the suspension via vacuum filtration, and rinsed with n-heptane twice. The product was then placed in a vacuum oven and dried under reduced pressure at 40° C. to obtain the final product.

Example 5 Preparation of the Eutectic Crystal of the Complex Formed by Compound A and L-Proline Compound A (25.0 mg) was dissolved in ethyl acetate (1 mL) and heated to 40° C. with magnetic stirring until compound A fully dissolved. The solution was filtered with a 0.45 μm microporous membrane (nylon membrane) and the filtrate was placed on a heater at 35° C. An equimolar ratio of 1 mol/L a solution containing L-proline in 95% aqueous ethanol (53.4 μL) was added slowly under magnetic stirring. The solution turned turbid after 10 minutes magnetic stirring, and then the mixture was cooled down to room temperature at a rate of 10° C./h under stirring, meanwhile a large amount of white precipitate appeared. The precipitated white solid was isolated from the suspension via vacuum filtration, and rinsed with n-heptane once. The product was then placed in a vacuum oven and dried under reduced pressure at 40° C. to obtain the final product.

Example 6 Preparation of the Eutectic Crystal of the Complex Formed by Compound A and L-Proline Compound A (25.0 mg) was dissolved in ethyl acetate (1 mL) and heated to 45° C. with magnetic stirring until compound A fully dissolved. The solution was filtered with a 0.45 μm microporous membrane (nylon membrane) and the filtrate was placed on a heater at 45° C. A 2-fold molar ratio of 1 mol/L a solution containing L-proline in 95% aqueous ethanol (106.8 μL) was added slowly under magnetic stirring. The solution turned turbid after 15 minutes magnetic stirring, and then the mixture was cooled down to room temperature at a rate of 15° C./h under stirring, meanwhile a large amount of white precipitate appeared. The precipitated white solid was isolated from the suspension via vacuum filtration, and rinsed with n-heptane twice. The product was then placed in a vacuum oven and dried under reduced pressure at 40° C. to obtain the final product.

Example 7 Preparation of the Eutectic Crystal of the Complex Formed by Compound A and L-Proline Compound A (100.4 mg) was dissolved in acetone (0.5 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (429 μL) was added slowly under magnetic stirring. The solution turned turbid and white solid began to precipitate after 20 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (46.9 mg, yield 31.3%).

Example 8 Preparation of the Eutectic Crystal of the Complex Formed by Compound A and L-Proline Compound A (250.4 mg) was dissolved in acetone (1 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1088 μL) was added slowly under magnetic stirring. The solution turned turbid and white solid began to precipitate after 15 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (331.8 mg, yield 88.8%).

Example 9 Preparation of the Eutectic Crystal of the Complex Formed by Compound A and L-Proline Compound A (250.9 mg) was dissolved in acetone (1 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1090 μL) was added slowly under magnetic stirring. The solution turned turbid and white solid began to precipitate after 25 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (271.0 mg, yield 72.5%).

Example 10 Preparation of the Eutectic Crystal of the Complex Formed by Compound A and L-Proline Compound A (250.9 mg) was dissolved in acetone (1 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1090 μL) was added slowly under magnetic stirring. The solution turned turbid and white solid began to precipitate after 25 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (271.0 mg, yield 72.5%).

Example 11 Preparation of the Eutectic Crystal of the Complex Formed by Compound A and L-Proline Compound A (100.7 mg) was dissolved in acetone (0.5 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (433 μL) was added slowly under magnetic stirring. The solution turned turbid and white solid began to precipitate after 25 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (93.6 mg, yield 64.4%).

Example 12 Preparation of the Eutectic Crystal of the Complex Formed by Compound A and L-Proline Compound A (100.8 mg) was dissolved in acetone (0.5 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (433 μL) was added slowly under magnetic stirring. The solution turned turbid and white solid began to precipitate after 25 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (107.8 mg, yield 71.4%).

Example 13 Preparation of the Eutectic Crystal of the Complex Formed by Compound A and L-Proline Compound A (200.4 mg) was dissolved in acetone (1.2 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (856 μL) was added slowly under magnetic stirring. The solution turned turbid and white solid began to precipitate after 25 minutes magnetic stirring, and then the mixture was cooled quickly with an ice-bath for 10 mins and white precipitate appeared. The precipitated white solid was isolated from the suspension via vacuum filtration, and rinsed with n-heptane three times. The product was then placed in a vacuum oven and dried under reduced pressure at 40° C. to obtain the final product.

Example 14 Preparation of the Eutectic Crystal of the Complex Formed by Compound A and L-Proline Compound A (272.3 mg) was dissolved in acetone (3.6 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1164 μL) was added slowly under magnetic stirring. The solution turned turbid and white solid began to precipitate after 10 minutes magnetic stirring, and then the mixture was cooled down to room temperature at a rate of 5° C./h under stirring, meanwhile white precipitate appeared. The precipitated white solid was isolated from the suspension via vacuum filtration, and rinsed with n-heptane three times. The product was then placed in a vacuum oven and dried under reduced pressure at 40° C. to obtain the final product (327.8 mg, yield 80.6%).

Example 15 Preparation of the Eutectic Crystal of the Complex Formed by Compound A and L-Proline Compound A (400.6 mg) was dissolved in acetone (4.8 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1712 μL) was added slowly under magnetic stirring. The solution turned turbid after 10 minutes magnetic stirring and a lot of white solid precipitated after another 0.5 min, and then the mixture was cooled down to room temperature at a rate of 20° C./h under magnetic stirring. The precipitated white solid was isolated from the suspension via vacuum filtration, and rinsed with n-heptane three times. The product was then placed in a vacuum oven and dried under reduced pressure at 40° C. to obtain the final product (461 mg, yield 77.1%).

Example 16 Preparation of the Eutectic Crystal of the Complex Formed by Compound A and L-Proline Compound A (589 mg) was dissolved in acetone (7.068 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (2977 μL) was added slowly under magnetic stirring. The solution turned turbid after 1 minute magnetic stirring and a lot of white solid began to precipitate, and then the mixture was cooled down to room temperature at a rate of 20° C./h under magnetic stirring. The precipitated white solid was isolated from the suspension via vacuum filtration, and rinsed with n-heptane three times. The product was then placed in a vacuum oven and dried under reduced pressure at 40° C. to obtain the final product.

Example 17 Preparation of the Eutectic Crystal of the Complex Formed by Compound A and L-Proline Compound A (407.52 mg) was dissolved in acetone (4.8 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1742 μL) was added slowly under magnetic stirring. The solution turned turbid after 1 minute magnetic stirring and a lot of white solid began to precipitate after another 1 minute, and then the mixture was cooled down to room temperature at a rate of 10° C./h under magnetic stirring. The precipitated white solid was isolated from the suspension via vacuum filtration, and rinsed with n-heptane three times. The product was then placed in a vacuum oven and dried under reduced pressure at 40° C. to obtain the final product (476.75 mg, yield 78.4%).

Example 18 Preparation of the Eutectic Crystal of the Complex Formed by Compound A and L-Proline Compound A (410.5 mg) was dissolved in acetone (4.8 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1754 μL) was added slowly under magnetic stirring. The solution turned turbid after 1 minute magnetic stirring and a lot of white solid began to precipitate after another 1 min, and then the mixture was cooled down to room temperature at a rate of 10° C./h under magnetic stirring. The precipitated white solid was isolated from the suspension via vacuum filtration, and rinsed with n-heptane three times. The product was then placed in a vacuum oven and dried under reduced pressure at 40° C. to obtain the final product (445.98 mg, yield 72.8%).

Example 19 Preparation of the Eutectic Crystal of the Complex Formed by Compound A and L-Proline Compound A (404.52 mg) was dissolved in acetone (4.8 mL) and heated to 55° C. with magnetic stirring until compound A fully dissolved. The solution was filtered with a 0.45 μm microporous membrane (nylon membrane) and the filtrate was placed on a heater at 55° C. A 2-fold molar ratio of 1 mol/L a solution containing L-proline in 95% aqueous ethanol (1729 μL) was added slowly under magnetic stirring. The solution turned turbid after 1 minute magnetic stirring and a lot of white solid began to precipitate, and then the mixture was cooled down to room temperature at a rate of 20° C./h under magnetic stirring. The precipitated white solid was isolated from the suspension via vacuum filtration, and rinsed with n-heptane three times. The product was then placed in a vacuum oven and dried under reduced pressure at 40° C. to obtain the final product (437.95 mg, yield 72.6%).

Comparative Example 1 Preparation of the Eutectic Crystal of the Complex Formed by Compound A and L-Proline Compound A (102.0 mg) was dissolved in isopropyl alcohol (0.5 mL) and heated to 80° C. with magnetic stirring until compound A fully dissolved. The solution was filtered with a 0.45 μm microporous membrane (nylon membrane) and the filtrate was placed on a heater at 80° C. A 2-fold molar ratio of 1 mol/L a solution containing L-proline in 95% aqueous ethanol (436 μL) was added slowly under magnetic stirring. The solution was clear after 1 h magnetic stirring, and then the mixture was cooled down to room temperature at a rate of 10° C./h under magnetic stirring. The solution turned turbid and little amount of white solid began to precipitate after stirring for 12 hours at room temperature. However, the mixture became clear when stirring stopped and small amount of oil was observed floating on the surface of the solution. There was no solid observed after the mixture was stored at 4° C. for 12 hours.

From the above comparative example 1, the eutectic crystal of the complex formed by compound A and L-proline could not be obtained if isopropyl alcohol was used as a solvent for dissolving compound A, even other conditions strictly followed the previously described preparation method in the present invention. It proved that the solvent for dissolving compound A was a key factor for the preparation method. The solvent should be not only a good solvent for dissolving compound A, but also a solvent miscible with 95% aqueous ethanol.

Effect Example 1 Identification of X-Ray Powder Diffraction

1. Samples: Eutectic crystal of the complex formed by compound A and L-proline prepared in example 1-19 and compound A.
2. Parameters of X-ray powder diffraction: A Cu-K$\alpha_1$ source (=1.54056 angstrom); Operating Voltage: 40 kV; Operating Current: 40 mA; Detector: PSD Detector; Scans Angle: 4-40 degrees (2-theta); Step value: 0.05°; Scanning Speed: 0.5 sec/step.
3. Experimental result The X-ray powder diffraction diagram of the eutectic crystal of the complex formed by compound A and L-proline prepared in example 1-19 is shown in FIG. 1. It can be seen from FIG. 1 that the diffraction peaks of the eutectic crystal of the complex formed by compound A and L-proline were selected from the following peaks: diffraction angle 2θ=4.339, 11.499, 12.835, 13.921, 15.294, 16.212, 16.804, 17.154, 18.335, 19.274, 19.982, 22.710, 23.218, 24.885, 27.940, 29.612 and 30.313 degrees. Peaks corresponding to marked numerals in FIG. 1 are shown in Table 1:

TABLE 1

| Peak number | 2θ value |
|---|---|
| 1 | 4.339 |
| 2 | 11.499 |
| 3 | 12.835 |
| 4 | 13.921 |
| 5 | 15.294 |
| 6 | 16.212 |
| 7 | 16.804 |
| 8 | 17.154 |
| 9 | 18.335 |
| 10 | 19.274 |
| 11 | 19.982 |
| 12 | 22.710 |
| 13 | 23.218 |
| 14 | 24.885 |
| 15 | 27.940 |
| 16 | 29.612 |
| 17 | 30.313 |

Figure 2:
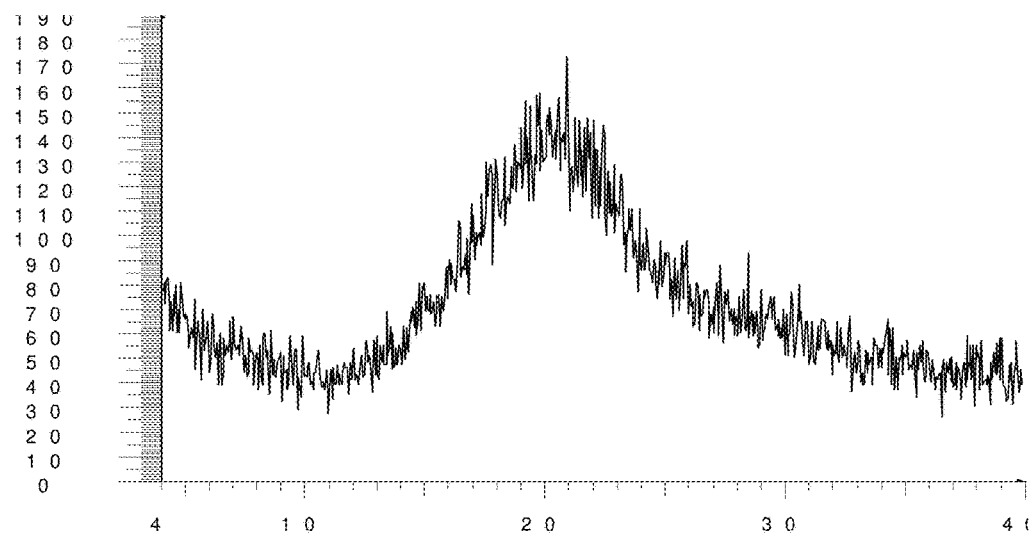
FIG. 2 is the X-ray powder diffraction diagram of compound A in effect example 1.

The X-ray powder diffraction diagram of starting material compound A is shown in FIG. 2. It can be seen from FIG. 2 that there is no obvious diffraction peaks in the X-ray powder diffraction diagram of starting material compound A, which means that starting material compound A is amorphous.

Effect Example 2 Polarized Light Microscopy

Figure 3:
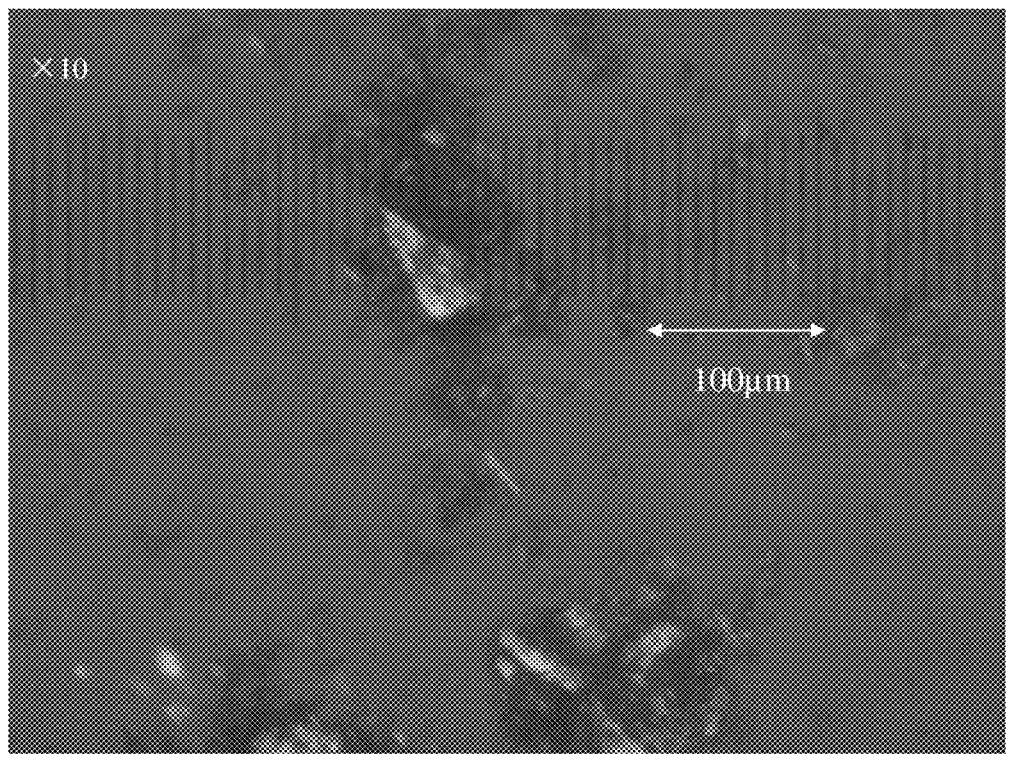
FIG. 3 is the polarizing light microscope photos of the eutectic crystal of the complex formed by compound A and L-proline in effect example 2.

1. Samples: Eutectic crystal of the complex formed by compound A and L-proline prepared in example 1-19 and compound A.
2. Parameters of Polarized light microscopy: Eyepiece 10×, Objective 10×.
3. Experimental result The polarizing light microscope photo of the eutectic crystal of the complex formed by compound A and L-proline prepared in example 1-19 is shown in FIG. 3. It can be seen from FIG. 3 that the eutectic crystal has obvious birefringence and shows a crystal habit of irregular particle. The particle size distributes in the range from 10 μm to 50 μm.

Figure 4:
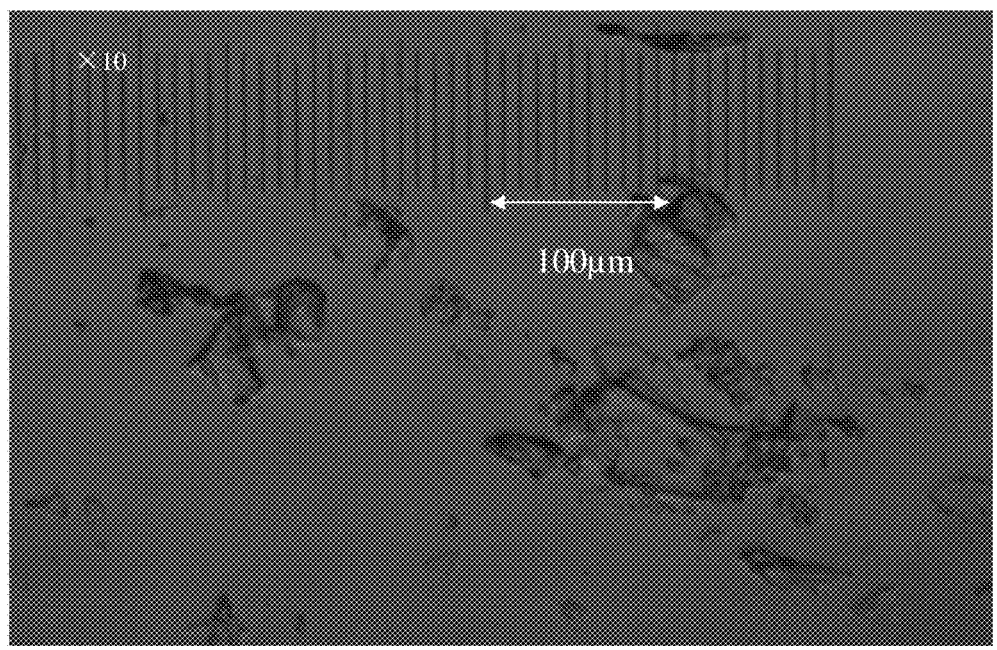
FIG. 4 is the polarizing light microscope photos of compound A in effect example 2.

The polarizing light microscope photo of starting material compound A is shown in FIG. 4. Compound A has no birefringence phenomenon and is in irregular glass state.

It can be seen from above comparison that comparing with the amorphous compound A, the eutectic crystal of the complex formed by compound A and L-proline of the present invention with a particle form has better stability and is conducive to the process for pharmaceutical preparation.

Effect Example 3 Dynamic Vapor Sorption Test

Figure 5:
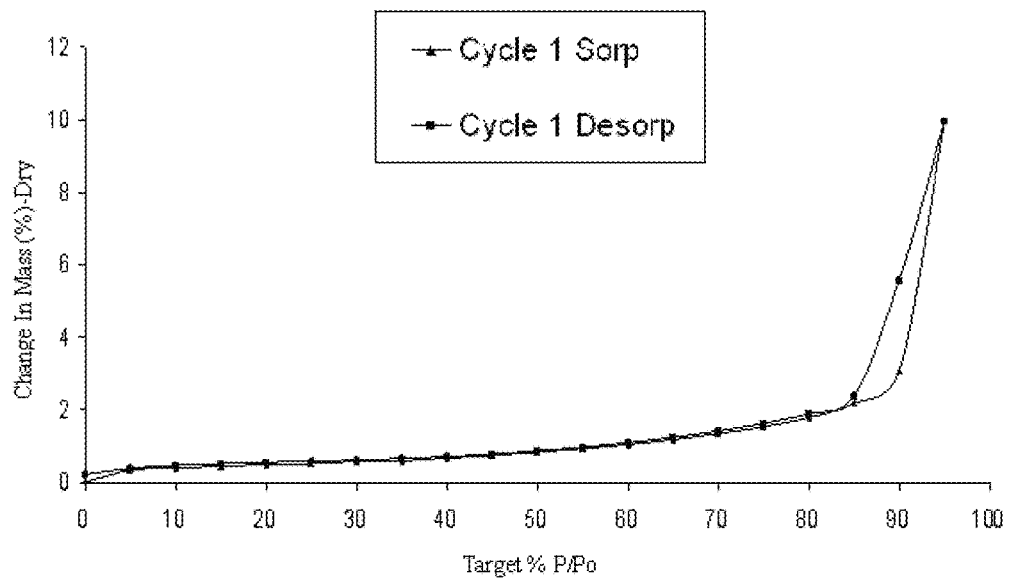
FIG. 5 is the dynamic vapor sorption isotherm of the eutectic crystal of the complex formed by compound A and L-proline in effect example 3.

1. Samples: Eutectic crystal of the complex formed by compound A and L-proline prepared in example 1-19 and compound A.
2. Parameters of dynamic vapor sorption test: The instrument: a dynamic moisture absorption analyzer (DVS Advantage, Surface Measurement System Ltd); Experimental temperature: 25° C.; Adsorption range: 0-95% relative humidity; Step interval: 5% relative humidity; Balance standard of weight gain: less than 0.01% weight change in 5 minutes; Longest time of balance: 120 minutes.
3. Experimental result The dynamic vapor sorption isotherm of the eutectic crystal of the complex formed by compound A and L-proline prepared in example 1-19 is shown in FIG. 5. It can be seen in FIG. 5 that when an initial mass is 10.2006 mg and relative humidity is increased from 0% to 85% RH, L-proline eutectic crystal absorbs moisture slowly and the moisture absorbed is only 2.174%, while RH is 95%, the weight increased finally is about 9.967%, which indicates that the eutectic crystal of the complex formed by compound A and L-proline is not very sensitive to moisture under normal conditions. In FIG. 5, Y axis is the weight gain percentage of the sample against its dry weight. In FIG. 5, relative humidity is defined as the ratio of the vapor pressure of water in air to the saturated vapor pressure of water.

Figure 6:
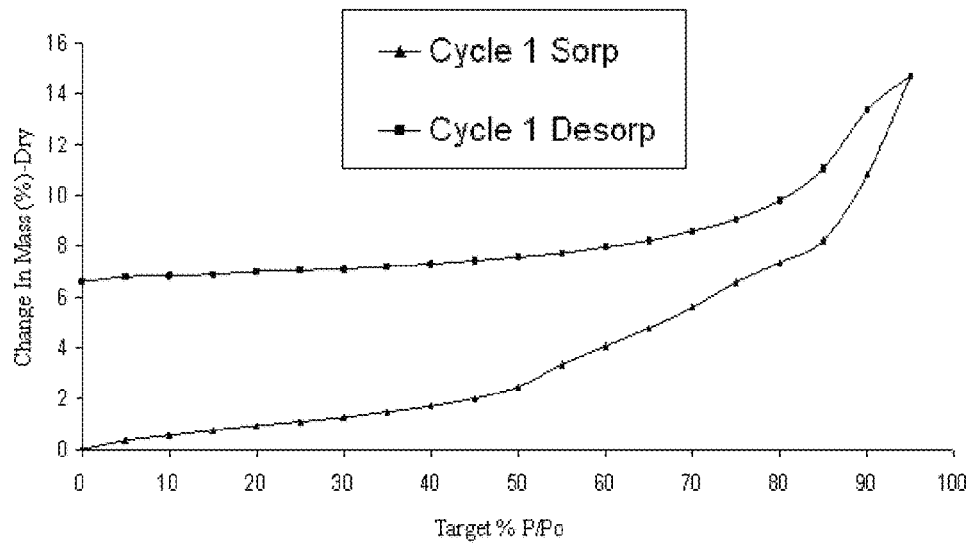
FIG. 6 is the dynamic vapor sorption isotherm of compound A in effect example 3.

The dynamic vapor sorption isotherm of compound A is shown in FIG. 6. It can be seen in FIG. 6 that when an initial mass is 10.3109 mg and relative humidity is 50%, the moisture absorption rate of compound A significantly accelerates, the moisture absorbed is about 4.8%, and it keeps absorbing moisture rapidly, the weight increased finally is 14.72% when the relative humidity reaches 95% RH. Thus, compound A is sensitive to moisture. In FIG. 6, Y axis is the weight gain percentage of the sample against its dry weight. In FIG. 6, relative humidity is defined as the ratio of the vapor pressure of water in air to the saturated vapor pressure of water.

It can be seen from above comparison that the eutectic crystal of the complex formed by compound A and L-proline of the present invention has low hygroscopicity, which shows obvious advantages.

Effect Example 4 Solubility Test

1. Samples: Eutectic crystal of the complex formed by compound A and L-proline prepared in example 1-19 and compound A.

2. Solubility test method: 2-3 mg sample was accurately weighed and put into a small vial, the right amount of ultra-pure water was added to make a target concentration of 2.0 mg/mL, the vial was rotated for 18 hrs at 25° C. till no changes of solubility, HPLC was used to determine the drug concentration, the solubility of the drug was calculated by preparing standard curve.

HPLC measurement condition: Instrument: Agilent 1200 HPLC; Chromatographic column: Zorbax SB-C8 (3.5 μm, 4.6×75 mm), SN: USEB009791; Mobile phase A: 10 mmol/L aqueous ammonium acetate solution (0.77 g of ammonium acetate was mixed evenly with 1 L of Milli-Q water), Mobile phase B: Acetonitrile, Mobile phase A: Mobile phase B=65:35 (v:v); Column temperature: 25° C.; Wave length: 220 nm; Sampling volume: 10 μL; Flow velocity: 1 mL/min; Detection time: 5 min, $t_0$=0.65 min, $t_R$=2.7 min, K'=3.15 (capacity factor, this value should be greater than 2), tailing factor=1.1.

3. Experimental result

TABLE 2 solubility of Eutectic crystal of the compound A and L-proline in different aqueous medium

| Medium | Mass (mg) | Volume (mL) | Target concentration (mg/mL) | Visual solubility | pH (after filtration) | Solubility measured by HPLC (mg/mL) |
|---|---|---|---|---|---|---|
| Water | 2.113 | 1.056 | 2.000 | clear | 7.941 | 1.94 |
| 0.1N HCl | 1.882 | 0.941 | 2.000 | clear | 0.975 | 1.91 |
| pH 2 | 1.724 | 0.862 | 2.000 | clear | 1.963 | 1.93 |
| pH 4 | 2.162 | 1.080 | 2.000 | clear | 4.610 | 1.93 |
| pH 6 | 1.977 | 0.988 | 2.000 | clear | 6.481 | 1.93 |
| pH 8 | 1.714 | 0.857 | 2.000 | clear | 8.060 | 1.93 |
| SGF | 1.638 | 0.819 | 2.000 | clear | 2.871 | 1.85 |
| SIF-Fasted | 1.758 | 0.879 | 2.000 | clear | 6.533 | 1.98 |
| SIF-Fed | 2.057 | 1.028 | 2.000 | clear | 4.956 | 2.08 |

TABLE 3 solubility of compound A in different aqueous medium

| Medium | Mass (mg) | Volume (mL) | Target concentration (mg/mL) | Visual solubility | pH (after filtration) | Solubility measured by HPLC (mg/mL) |
|---|---|---|---|---|---|---|
| Water | 3.102 | 1.552 | 2.000 | clear | 8.540 | 1.68 |
| 0.1N HCl | 3.190 | 1.596 | 2.000 | clear | 2.182 | 1.56 |
| pH 2 | 2.952 | 1.476 | 2.000 | clear | 2.151 | 1.61 |
| pH 4 | 3.298 | 1.648 | 2.000 | clear | 5.094 | 1.64 |
| pH 6 | 2.802 | 1.400 | 2.000 | clear | 6.180 | 1.64 |
| pH 8 | 3.194 | 1.596 | 2.000 | clear | 8.020 | 1.57 |
| SGF | 2.634 | 1.316 | 2.000 | clear | 2.178 | 1.91 |
| SIF-Fasted | 2.776 | 1.388 | 2.000 | clear | 6.146 | 2.04 |
| SIF-Fed | 3.433 | 1.716 | 2.000 | clear | 5.099 | 1.92 |

Wherein, SGF refers to manual mode gastric juice, SIF-Fasted refers to simulation intestinal juice (before meal), SIF-Fed refers to simulation intestinal juice (after meal).

What is claimed is:

1. A eutectic crystal of a complex represented by formula I formed by a glucose derivative and L-proline, wherein the complex is composed of compound A represented by formula A and L-proline, and wherein the molar ratio of compound A to L-proline in the complex is 1:2;

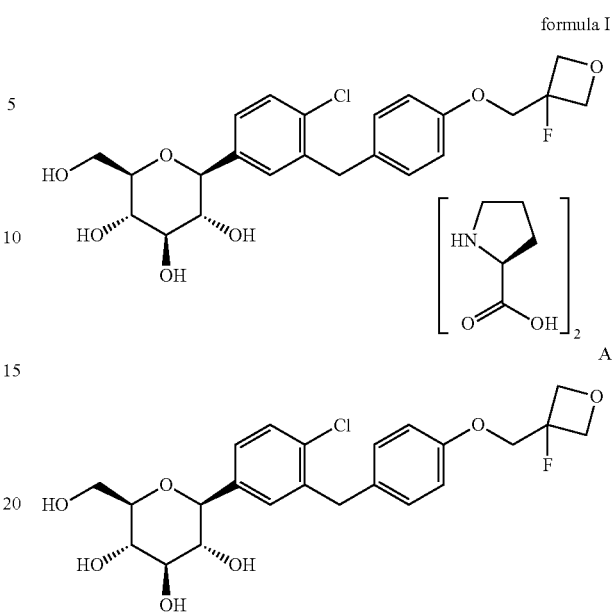

formula I and wherein an X-ray powder diffraction diagram of the eutectic crystal, when the diffraction angle is 2θ and under Cu-Kα1 radiation, shows characterized peaks at:
4.339±0.1, 15.294±0.1, 16.804±0.1, 18.335±0.1, 19.274±0.1, 19.982±0.1, 23.218±0.1 and 24.885±0.1; or
4.339±0.1, 11.499±0.1, 12.835±0.1, 13.921±0.1, 15.294±0.1, 16.212±0.1, 16.804±0.1, 17.154±0.1, 18.335±0.1, 19.274±0.1, 19.982±0.1, 22.710±0.1, 23.218±0.1, 24.885±0.1, 27.940±0.1, 29.612±0.1 and 30.313±0.1.

2. The eutectic crystal of claim 1, wherein an X-ray powder diffraction diagram of the eutectic crystal shows characterized peaks at 4.339±0.1, 15.294±0.1, 16.804±0.1, 18.335±0.1, 19.274±0.1, 19.982±0.1, 23.218±0.1 and 24.885±0.1 when the diffraction angle is 2θ and under Cu-Kα1 radiation.

3. The eutectic crystal of claim 1, wherein an X-ray powder diffraction diagram of the eutectic crystal shows characterized peaks at 4.339±0.1, 11.499±0.1, 12.835±0.1, 13.921±0.1, 15.294±0.1, 16.212±0.1, 16.804±0.1, 17.154±0.1, 18.335±0.1, 19.274±0.1, 19.982±0.1, 22.710±0.1, 23.218±0.1, 24.885±0.1, 27.940±0.1, 29.612±0.1 and 30.313±0.1 when the diffraction angle is 2θ and under Cu-Kα1 radiation.

4. A preparation method for preparing the eutectic crystal of claim 1, comprising the following steps: mixing a solution containing compound A and a solvent with a solution containing L-proline and a solvent at a temperature of from 30° C.-80° C., cooling the resulting mixture and crystallizing the resulting cooled mixture; wherein the solvent in the solution containing compound A is selected from the group consisting of acetone, ethyl acetate and acetonitrile; and wherein the solvent in the solution containing L-proline is 95% aqueous ethanol.

5. The preparation method of claim 4, further comprising, before mixing with the solution containing L-proline, filtering the solution containing compound A with a microporous membrane, and then mixing the resulting filtrate containing compound A with the solution containing L-proline; wherein the microporous membrane is a nylon membrane with a pore size of 0.45 μm.

6. The preparation method of claim 4, wherein the mixing of the solution containing compound A with the solution containing L-proline is at a temperature of 55° C.-65° C.

7. The preparation method of claim 4, wherein the concentration of compound A in the solution containing compound A is 25 mg/mL-400 mg/mL; and the amount of the 95% aqueous ethanol in the solution containing L-proline is 90 mg/mL-120 mg/mL relative to the mass of L-proline in the solution containing L-proline.

8. The preparation method of claim 4, wherein the molar ratio of L-proline in the solution containing L-proline to compound A in the solution containing compound A is in the range of from 1:1 to 2:1; the mixing of the solution containing compound A with the solution containing L-proline is by vortex mixing, magnetic mixing or turbulence mixing; the mixing of the solution containing compound A with the solution containing L-proline lasts for 1-30 mins; and the cooling results in cooling to a temperature between 10° C. and less than 30° C.

9. The preparation method of claim 4, wherein the cooling is conducted at a rate of 1-20° C./h.

10. The preparation method of claim 9, wherein the cooling is conducted at a rate of 5-10° C./h.

11. The preparation method of claim 4, wherein the cooling and crystallizing are carried out under stirring.

* * * * *